United States Patent [19]

Sibley et al.

[11] Patent Number: 5,552,289

[45] Date of Patent: Sep. 3, 1996

[54] CDNA ENCODING THE LONG ISOFORM OF THE $D_2$ DOPAMINE RECEPTOR

[75] Inventors: David R. Sibley, Rockville; Frederick J. Monsma, Jr., Baltimore; Loris D. McVittie; Lawrence C. Mahan, both of Bethesda, all of Md.

[73] Assignee: United States of America, Washington, D.C.

[21] Appl. No.: 102,594

[22] Filed: Aug. 3, 1993

Related U.S. Application Data

[60] Continuation of Ser. No. 838,931, Feb. 21, 1992, abandoned, which is a division of Ser. No. 430,049, Nov. 1, 1989, Pat. No. 5,128,254.

[51] Int. Cl.$^6$ ............................................... G01N 33/567
[52] U.S. Cl. ............................................................ 435/7.21
[58] Field of Search .............................. 435/6, 7.1, 172.3, 435/7.21

[56] References Cited

PUBLICATIONS

Ohara, et al.; The Interaction Between D-2 Dopamine Receptors and GTP-Binding Proteins; Molecular Pharmacology; vol. 33, pp. 290–296; 1988.

Bunzow, et. al. "Cloning and Expression Of A Rat $D_2$ Dopamine Receptor cDNA." Nature, vol. 336, pp. 783–787, 22/29 Dec. 1988.

*Primary Examiner*—George C. Elliott
*Attorney, Agent, or Firm*—Knobbe Martens Olson & Bear

[57] ABSTRACT

In the present investigation, we report the identification and cloning of a cDNA encoding an RNA splice variant of the rat $D_2$ receptor cDNA$^{12}$. This cDNA codes for a receptor isoform which is predominantly expressed in the brain and contains an additional 29 amino acids in the 3rd cytoplasmic loop, a region believed to be involved with G protein coupling. This is the first example of a novel G-protein coupled receptor isoform generated by alternative RNA splicing.

3 Claims, 4 Drawing Sheets

```
 976 GAG AAG AAT GGG CAC GCC AAG ATT GTC AAT CCC AGG ATT GCC AAG TTC TTT GAG ATC CAG ACC ATG CCC AAT GGC 350
     Glu Lys Asn Gly His Ala Lys Ile Val Asn Pro Arg Ile Ala Lys Phe Phe Glu Ile Gln Thr Met Pro Asn Gly
1051 AAA ACC CGG ACC TCC CTT AAG ACG ATG AGC AGA AAG CTC TCC CAG CAG AAG GAG AAA GCC ACT CAG ATG 375
     Lys Thr Arg Thr Ser Leu Lys Thr Met Ser Arg Arg Leu Ser Gln Gln Lys Glu Lys Ala Thr Gln Met
1126 CTT GCC ATT GTT CTC GGT GTG TTC TTC ATC ATC TGC CTG CCC TTC TGG TGG CTG CCC TTC ATC ACG CAC ATC CTG AAT ATA CAC TGT 400
     Leu Ala Ile Val Leu Gly Val Phe Phe Ile Ile Cys Leu Pro Phe Trp Leu Pro Phe Ile Thr His Ile Leu Asn Ile His Cys
1201 GAT TGC AAC ATC CCA CCA GTC CTC TAC AGC GCC TTC ACA TGG CTG TAT GTC AAC AGT GCC GTC AAC CCC ATC 425
     Asp Cys Asn Ile Pro Pro Val Leu Tyr Ser Ala Phe Thr Trp Leu Tyr Val Asn Ser Ala Val Asn Pro Ile
1276 ATC TAC ACC ACC TTC AAC ATC GAG ATC CGC AAG TTC CGC AAG ATC TTG ATG AAG CTC TTG ATG AAG TGC TGC TGA GTC TGC CCC TTG CCT GCA CAG 444
     Ile Tyr Thr Thr Phe Asn Ile Glu Ile Arg Lys Phe Arg Lys Ile Leu Met Lys Leu Met Lys Leu His Cys
1357 CAGCTGCTTCCCACCTCCCTGCCTATGCGAGCAGGCCCAGACCTCATCCCTGCCAAGCTGTGGGCAGAAAGGCCCAGATGGACTTGGCCTTCTCTCGACCCTGCAG
1457 GCCCTGACGTCAGTGTTAGCTTGGCTCGATGCCCCTCTCTGCCCACACACCCCTCATCCTGCCCAGGGTAGGCCAGGGAGACTGGTATCTTACCAGCTCTGGGGT
1557 TGGACCCATGGCTCAGGGCAGCTGCCACAGAGTGCCCCTCTCTCATATCCAGAGACCCTGTGTCTCCTTGGCACCAAAGATGCAGCGGCCTTCCTTGACCTTCCTCTT
1657 GGGCACAGAAACTAGCTCAGTGGTCGAGACACCCTGTGCCTTGGCCTGGCCCTTGCTGTGCCAGATCAGGTGTGGGAGGGAGCAACAG
1757 TTCTTACTTTATAGGAACCAGGGAAAGCAGGGAACACGCCAAGTCCTCCAGCAACATCAGTGTCAGGAGACACACATCAGTGTATTACTATGTCCTACCTTG
1857 GGACCCCAGAGAAACTGAGGCTGAAAAATCTGTTTTCCACTCCAACTCTAGTGTGAGTCCCTACTTTCATAGCCATGGGTATTACTATGTCCTACCTTG
1957 TTATAGTATCCATGGGTTTCTGTACCCTTTGGGGAAAAACAACTCTAATCCTCAAGGGCCCCAAGAGAATCTGTAAGGAGAAAATAGGCTGATCTCC
2057 CTCTACTCTCCAATCCACTCCACCACTTCCTTGATGATGTATCCATTCCTCACAGCAAATGCTGGCCAGTCAGCCTTGGACCAGTGTTGGAG
2157 TTGAAGCTGGATGTGGTAACTTGGGTCTCTTTGGGCTCTTGGGCTGTGTTAACATCGTCTCTCCATATCTCTTCCTTCCCAGTGCCTCTGCCTTAGA
2257 AGAGGCTGTGGATGGGGTGCTGGGACTGCTGATACCATTGGGCCTGGCCCTGAATGAGGAGGGAAGCTGCAGTTTGGAGGGTTCTCGGGATCCAACTCTG
2357 TAACATCACTATACCTGCACCAAAACTAATAAAACCTTGACAAGAGTCAAAAAAAAAA

2404
```

CDNA ENCODING THE LONG ISOFORM OF THE D₂ DOPAMINE RECEPTOR

This application is a continuation of application Ser. No. 07/838,931, filed Feb. 21, 1992, now abandoned which is a division of application Ser. No. 07/430,049, filed Nov. 1, 1989 now U.S. Pat. No. 5,128,254.

BACKGROUND OF THE INVENTION

The present invention relates to a DNA segment encoding a long isoform of a mammalian $D_2$ dopamine receptor having a sequence of 29 amino acids that is absent in the known isoform of this receptor.

Dopamine receptors belong to a large class of neurotransmitter and hormone receptors which are linked to their signal transduction pathways via guanine nucleotide binding regulatory (G) proteins. Pharmacological, biochemical and physiological criteria have been used to define two subcategories of dopamine receptors referred to as $D^1$ and $D_2$[1]. $D_1$ receptors are associated with the activation of adenylyl cyclase activity[2] and are coupled with the $G_s$ regulatory protein[3]. In contrast, activation of $D_2$ receptors results in various responses including inhibition of adenylyl cyclase activity[4], inhibition of phosphatidylinositol turnover[5], increase in $K^+$ channel activity[6] and inhibition of $Ca^{2+}$ mobilization[7]. The G protein(s) linking the $D_2$ receptors to these responses have not been identified, although $D_2$ receptors have been shown to both co-purify[8,9] and functionally reconstitute[10,11] with both "$G_i$" and "$G_o$" related proteins[3]. One means of achieving the diversity of second messenger pathways associated with $D_2$ receptor activation would be the existence of multiple $D_2$ receptor subtypes, each being coupled with a different G protein-linked response. Efforts towards elucidating $D_2$ receptor diversity were recently advanced by the cloning of a cDNA encoding a rate $D_2$ receptor[12]. This receptor exhibits considerable amino acid homology with other members of the G protein-coupled receptor super-family for which cDNAs and/or genes have been cloned[12,13].

SUMMARY OF THE INVENTION

The present invention relates to a DNA segment encoding a long isoform of a mammalian $D_2$ dopamine receptor having a sequence of 29 amino acids that is absent in the known isoform of this receptor. This "long" isoform is the predominant species in mammalian tissues that are populated by $D_2$ dopamine receptors. In a principal embodiment, a recombinant DNA molecule comprising CDNA clone of the rat long isoform of this receptor and an expression vector is used to transfect eukaryotic cells which results in expression of this receptor on those cells. According to the present invention, receptors of this isoform, either in isolation or incorporated in cell membranes, are used for screening and developing drugs for selective activity on this dopamine receptor long isoform.

Further, the present embodiment of the DNA segment of this invention, which encodes the rat $D_2$ receptor long isoform, can be used for a nucleic acid probe in hybridization methods according to this invention to obtain molecular clones of DNA segments encoding the homologous receptors of this same isoform from any other mammalian species.

The present invention may be understood more readily by reference to the following detailed description of specific embodiments and the figures included therein, which illustrate the following:

BRIEF DESCRIPTION OF THE DRAWINGS

FIGS. 1A and 1B Nucleotide and deduced amino acid sequence of the $D_2$ receptor cDNA done. The 87 bp/29 amino acid insertion sequence is indicated by underlining. The nucleotide sequence is numbered beginning with the initiator methionine and indicated at the left of each line. The amino acid numbers are indicated at the right of each line. The single base differences in the 3' untranslated sequence are indicated by dots.

Figure 1A:
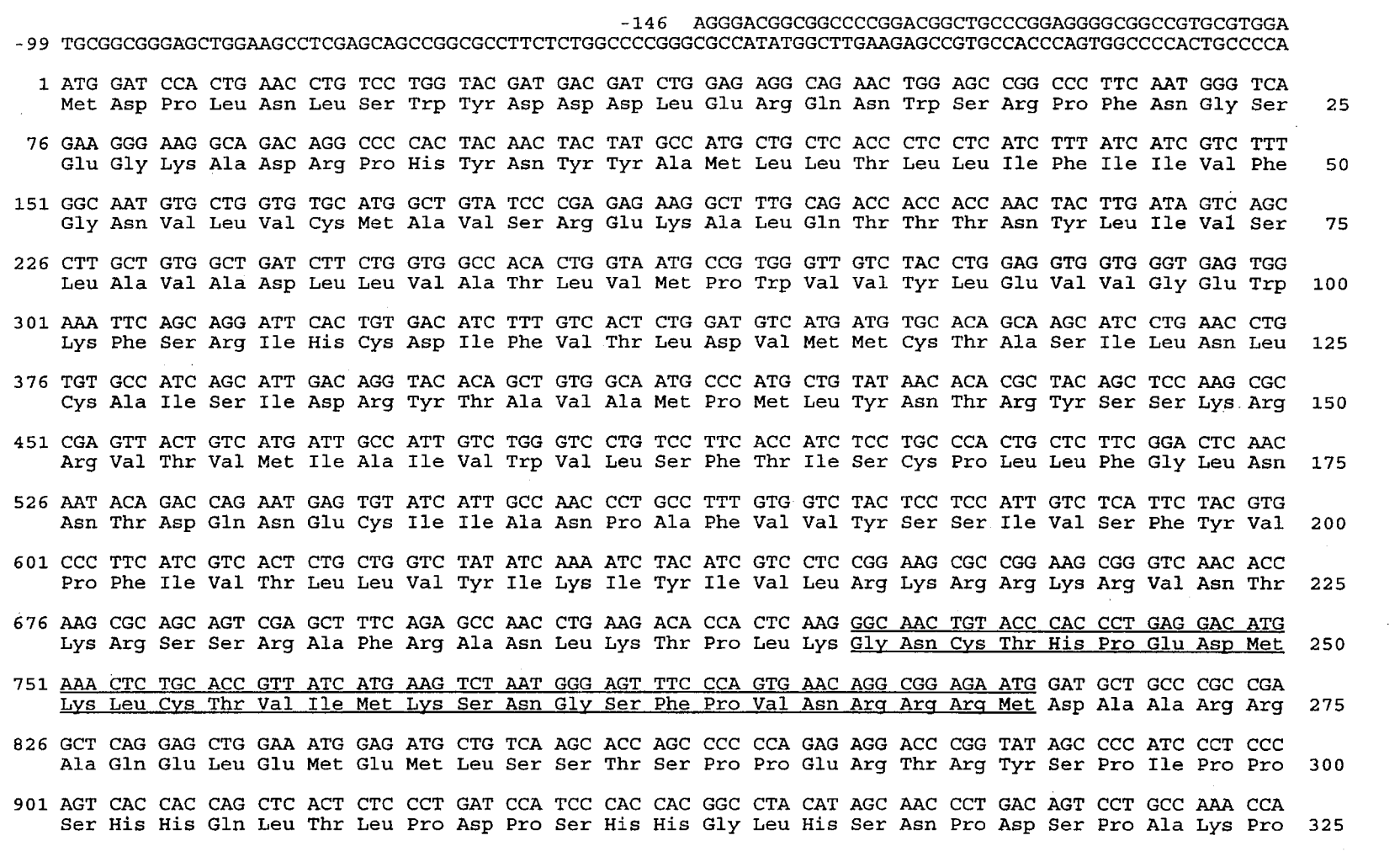
Figure 2A:
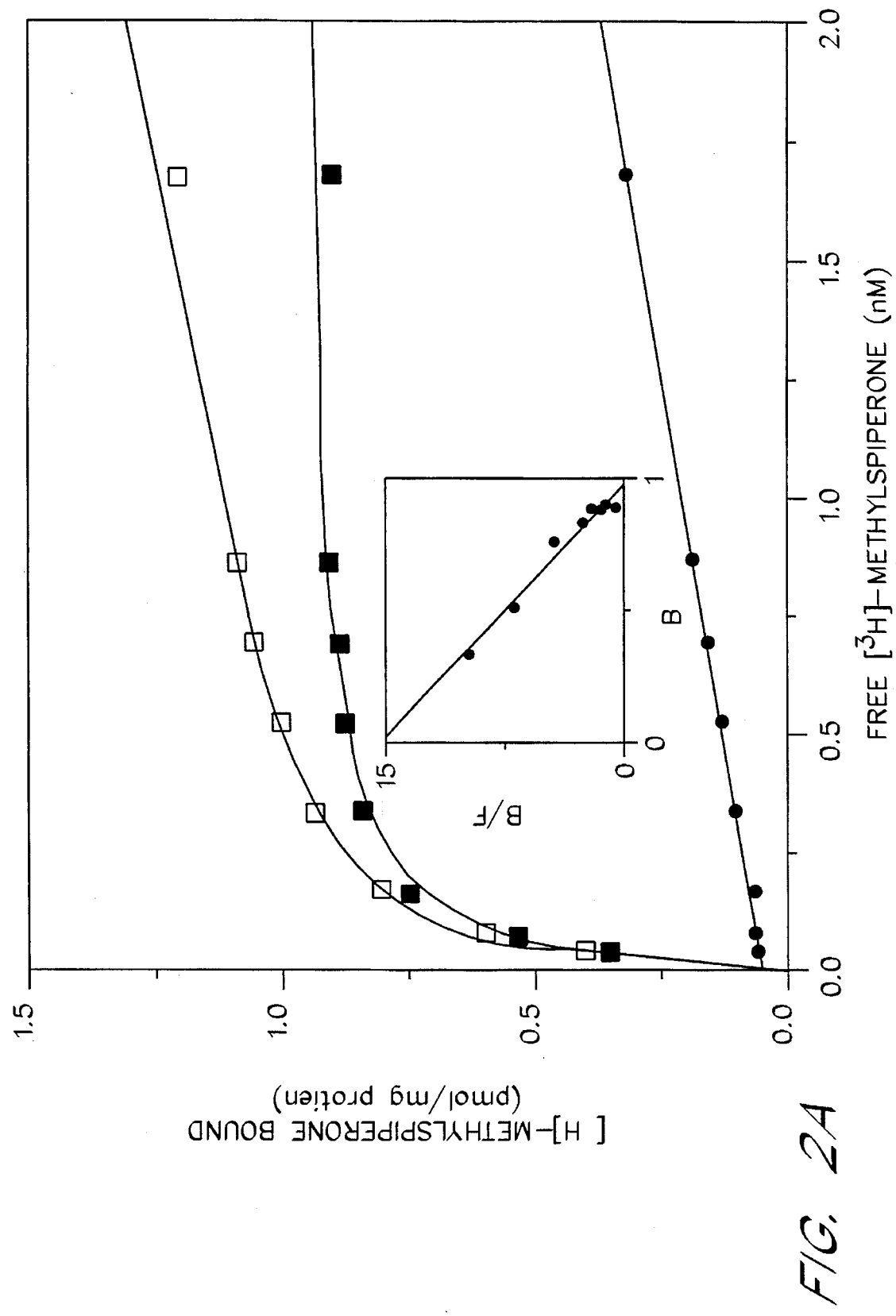
FIGS. 2A and 2B. Expression of the $D_2$ receptor cDNA in COS-7 cell membranes assayed with [³H]methylspiperone binding. 2A, Saturation isotherms of the total (□), nonspecific (●), and specific (o) binding of [³H]methylspiperone to transfected COS-7 cell membranes. The inset shows a Scatchard transformation of the specific binding data. In this experiment, which was representative of three, the calculated $K_D$ and $B_{max}$ values were 64.1 pM and 0.97 pmol/mg protein, respectively. 2B, Competition analysis of various dopaminergic ligands for [³H]methylspiperone binding in COS-7 cell membranes. In this experiment, [³H]methylspiperone (0.6 nM) was incubated with increasing concentrations of the following ligands: spiperone (▲), (+)butaclamol (△), (−)sulpiride (■), dopamine (●), SCH-23390 (□), and (−)butaclamol (o). Average $K_i$ and SEM values from 3 experiments are given in the text.

We conducted Northern blot analysis of $D_2$ receptor transcripts in brain and other rat tissues. Each lane contained 2 μg of poly (A)⁺RNA. Lanes 1, total brain; 2, cerebellum; 3, cortex; 4, hippocampus; 5, olfactory bulb; 6, mesencephalon; 7, retina; 8, kidney; 9, striatum; 10, pituitary. The gel locations of the RNA size markers (kb) are indicated. The blots were hybridized with an oligonucleotide derived from amino acids 10–25 (FIG. 1): 5'-TGACCCATTGAAGGGC-CGGCTCCAGTTCTGCTGCCTCTCCAGATCGTCATC-3', Hybridization was performed with an insert sequence oligonucleotide derived from amino acids 242–257 (FIG. 1): 5'-CATGATAACGGTGCAGAGTTTCATGTC-CTCAGGGTGGGTACAGTTGCC-3'. This experiment was performed twice with similar results.

Darkfield photomicrographs (silver grains appear white) of in situ hybridization histochemical (ISHH) localization of $D_2$ receptor mRNA in a coronal section of rat brain which includes the striatum. ISHH labeling using the ³⁵S-labeled oligonucleotide from FIG. 3a. 4B ISHH labeling using the ³⁵S-labeled oligonucleotide from FIG. 3b. In both sections the labeling of cells is most dense in the striatum and olfactory tubercle. High power magnification of labeling showed localization of $D_2$ receptor mRNA in a subset of medium sized neurons in the striatum. Approximately half of the medium sized cells are labeled by this procedure.

DESCRIPTION OF SPECIFIC EMBODIMENTS

As part of an effort to isolate oDNAs encoding dopamine receptor subtypes, we initially constructed a λZAP II cDNA library using mRNA purified from rat striatum, the region of the brain known to contain the highest levels of both $D_1$ and $D_2$ dopamine receptors[1]. Poly (A)+ RNA was isolated from rat striatal tissue using standard procedures[18] and used to construct a cDNA library in the λZAP II vector (Stratagene, La Jolla, Calif.). The resulting library contained 6.1×10⁶ independent recombinants. 1×10⁶ recombinants from the unamplified library were screened using the oligonucleotide 5'-GATGAAGAAGGGCAGCCAGCAGATGAT-GAACACA(G)CC-3' radiolabeled using [γ-³²P]ATP and T4 polynucleotide kinase. Duplicate nitrocellulose filters were hybridized in 0.3M NaCl/0.03M sodium citrate (2× SSC), 0.02M $Na_2HPO_4$, 0.1% SDS, 0.2 mg/ml salmon sperm DNA, and $4 \times 10^6$ dpm/ml of $^{32}P$-labeled probe for 18 hr at 42° C. High stringency washing of the filters was performed with 0.5× SSC and 0.1% SDS at 60° C. prior to autoradiography. λ phage found to hybridize to the probe were subsequently plaque purified. In vivo excision and rescue of the nested pBluescript plasmids from the λZAP II clones were performed using helper phage according to the stratagene protocol. Nucleotide sequence analysis was performed using the Sanger dideoxy nucleotide chain termination method on denatured double-stranded plasmid templates with Sequenase (US Bio-chemical Corp.). Primers were synthetic oligonucleotides which were either vector-specific or derived from prior sequence information. In some cases a series of nested deletion mutants were constructed using the EXO III/Mung Bean nuclease procedure (Stratagene) prior to DNA sequencing.

This library was screened with a mix of two 36mer synthetic oligonucleotides, the sequence of which was derived from amino acids 352–363 of the rat $D_2$ receptor cDNA[12]. This region corresponds to the 6th transmembrane spanning domain and is known to exhibit very high homology among previously cloned G protein-coupled receptors[13]. Out of $1 \times 10^6$ recombinants screened, a total of 15 positive clones were isolated. Restriction analysis and partial sequence information indicated that 5 of these clones were related to the rat $D^2$ receptor cDNA previously reported[12]. One of the clones containing an insert of 2.5 kb was completely sequenced and the nucleotide and deduced amino acid sequence of this cDNA is shown in FIG. 1A and 1B. The longest open reading frame in this cDNA codes for a 444 amino acid protein with a relative molecular mass Mr=50,887. The nucleotide and amino acid sequence within this coding region is identical to the rat $D_2$ receptor cDNA previously reported with the notable exception of an additional 87 bp sequence coding for a 29 amino acid insertion between residues 241 and 242[12]. This is located within the predicted 3rd cytoplasmic loop approximately 30 amino acids away from the carboxy terminus of the 5th transmembrane spanning domain. In addition to this insertion sequence, and a slightly extended, 5' untranslated sequence, we also noted 5 base differences within the 3' untranslated region in comparison with the previously published sequence[12] (FIG. 1A and 1B). Subsequent sequence analysis indicated that all 5 of the $D_2$ receptor-related cDNAs isolated from this library contained the identical 87 bp insertion sequence. The nucleotide sequences delineating the boundaries of this insertion sequence correspond with the consensus exon sequences for RNA splice junctions[14], suggesting that the cDNA resulted from alternative RNA splicing.

In order to confirm the $D_2$ subtype identity of this cDNA done and to determine if the 29 amino add insertion sequence results in a major alteration in the ligand binding properties of the $D_2$ receptor, the cDNA was inserted into the SV40 promoter-driven vector, pEUK-C1, for expression in eukaryotic cells.

Figure 2B:
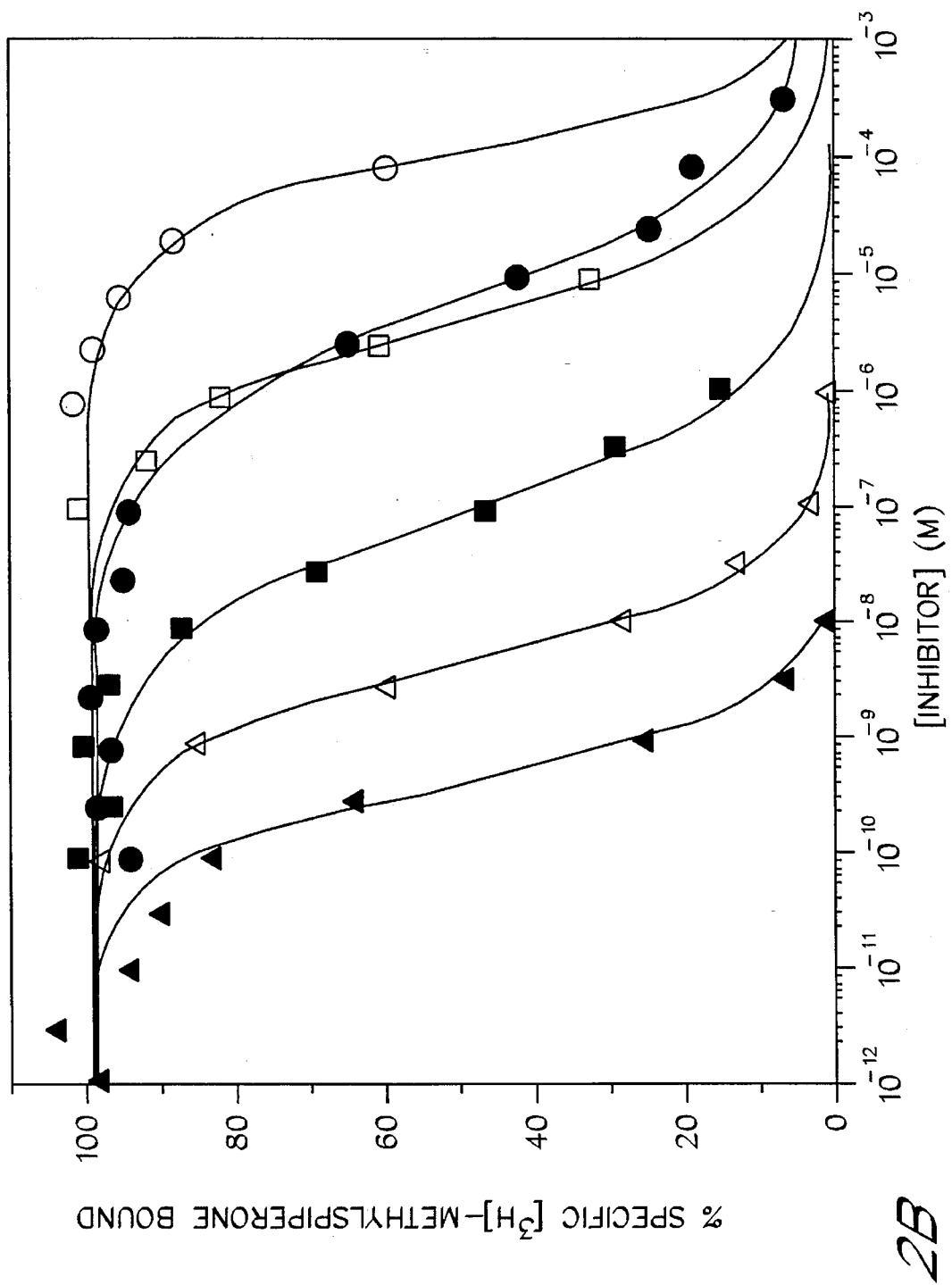

A 2.4-kb Xba I-Xho I fragment containing the entire coding region and most of the $D_2$ receptor cDNA was excised from the pBluescript clone and ligated into the corresponding restriction sites of the pEUK-C1 vector (Clonetec. Palo Alto, Calif.), The resulting plasmid, pEUK-D2L. was then transfected into COS-7 cells using a modified $CaPO_4$ precipitation method (Clonetech). The cells were treated with 3mM sodium butyrate after 48 hr and were harvested after 72 hr, Membranes were prepared and assayed for $D_2$ receptor binding activity using [$^3H$]methylspiperone (Dupont/NEN) exactly as previously described[20]. FIG. 2A shows that [$^3H$]methylspiperone bound to the membranes in a saturable fashion with high specific activity (=1 pmol/mg protein) and an affinity (62.1 ±2.1 pM) in good agreement with that found in the striatum[1]. No specific binding activity was detected in COS-7 cells that had not been transfected with pEUK-D2L or transfected with the pEUK-C1 vector alone (data not shown). FIG. 2B demonstrates the ability of a variety of dopaminergic ligands to compete for specific [$^3H$]methylspiperone binding to transfected COS-7 cell membranes. The high affinity $D_2$-selective antagonist, spiperone (36±3.8 pM) is the most potent agent followed by the nonselective dopaminergic antagonist (+)butaclamol (0.52 ±0.01 nM) which is more than 4 orders of magnitude more potent than its inactive isomer, (−)butaclamol (>10 μM). The $D_2$-selective antagonist (−)sulpiride (7.9±0.42 nM) also exhibits high affinity whereas the $D_1$-selective antagonist SCH-23390 (0.41±0.047 μM) does not. The rank order of potency as well as the absolute affinities ($K_i$) of the antagonists agree well with those previously demonstrated for $D_2$ receptors[1], Dopamine is also able to completely inhibit [$^3H$]methylspiperone binding ($K_i$=0.71±0.012 μM) although the competition curve is homogeneous (Hill coefficient=1) (FIG. 2B) and not significantly affected by guanine nucleotide,, (data not shown) indicating the absence of appropriate G protein coupling[15] in the COS-7 cells. These experiments indicate that the insertion sequence does not appear to affect the basic properties of ligand recognition for the $D_2$ receptor, In order to verify the expression of the $D_2$ receptor variant containing the insertion sequence and determine the relative proportions of the two receptor isoforms, we subjected various rat tissues to Northern blot analysis using an oligonucleotide probe to a consensus region as well as an insert sequence-specific probe.

Poly (A)+RNA was isolated from rat tissues using standard procedures[19] and run on 1% agarose plus 0.66M formaldehyde gels. After electrophoresis and blotting, the filters were prehybridized in 4× SSPE, 5× Denhardt's, 50% formamide, 250 μg/ml yeast +RNA, 500 μg/ml sheared salmon sperm DNA, and 0.1% SDS for 16 hr at 37° C. The filter blots were then hybridized in the same solution for 18 hr at 37° with $2 \times 10^6$ dpm/ml oligonucleotide probe radiolabeled with [α-32p]ATP and terminal deoxytranferase. The blots were washed in 1× SSPE and 0.1% SDS for 20 min for four times at 56° C. and twice at room temperature prior to autoradiography.

The tissues expressing the highest levels of the 2.9 kb $D_2$ receptor mRNA am the striatum and pituitary. The retina shows a moderate abundance of mRNA with low levels being observed in the mesencephalon and cortex and trace quantities detected in the olfactory bulb and hippocampus. Little to no mRNA was found in the cerebellum and kidney. This tissue distribution corresponds closely to that previously determined for $D_2$ receptor expression[1]. Of greatest interest, however, is the fact that in all of the tissues examined, the amount of mRNA detected with the two probes is very similar and in no instance did the consensus probe detect greater quantities of mRNA.

To further investigate the relative distributions of the two mRNAs encoding the $D_2$ receptor isoforms, we performed in situ hybridization analysis in the rat forebrain with the two oligonucleotide probes derived from amino acids 10–25 and 242–257 of FIG. 1. Darkfield photomicrographs of in situ hybridization histochemical localization of $D_2$ receptor mRNA in a coronal section of rat brain which includes the striatum.

Coronal sections through the striatum were cut in a cryostat and adhered to glass slides that had been twice coated with gelatin. Sections were fixed in a 4% paraformaldehyde solution in 0.9% saline for 10 min, rinsed and incubated in a fresh solution of 0.25% acetic anhydride in 0.1M triethanolamine and 0.9% saline (pH 8.0) for 10 min, dehydrated in ethanol and defatted for 2×5 min in chloroform, rehydrated and air dried. These sections were then hybridized with the $^{35}$S-dATP tailed oligonucleotide probes and processed as previously described[21]. Subsequently, the slides were dipped in NTB3 emulsion (diluted 1:1 with water) and exposed for 4–6 weeks, after which they were developed in D-19 developer for 2 min. fixed, rinsed, counterstained with thionin, dehydrated and coversliped out of xylene.

As can be seen, identical patterns of labeling were obtained using both the consensus region probe and the insert sequence probe. The highest labeling occurred in the striatal neurons where about 50% of the medium sized neurons were labeled. Larger sized neurons in the striatum also exhibited labeling (data not shown), It is interesting that there did not appear to be any difference in the levels of mRNA detected using the two oligonucleotide probes. If any tissue or brain area expressed mRNA containing the insertion sequence at a level equal to or less than the one lacking the insertion, then the consensus probe should detect mRNA levels that are at least 2-fold greater than those seen with the insert probe. These experiments thus indicate that not only is the longer $D_2$ receptor variant (which we propose designating $D_{2L}$) expressed in brain and other tissues, but in those areas which have been examined (especially the striatum), it appears to be the major if not exclusive isoform. Further experiments directed at determining the actual levels of the receptor proteins will be required to confirm this point. At present, the location of predominant expression of the shorter $D_2$ receptor lacking the insertion sequence (now designated $D_{2S}$) is unclear.

With the exception of the visual opsins, the genes for the G protein-coupled receptor family have, in most instances, demonstrated a lack of introns within their coding sequences[13] thus precluding the generation of receptor diversity through alternative RNA splicing. Recently, however, it has been determined that the serotonin $5HT_{1C}$ (B. J. Hoffman, personal communication) and $D_2$ dopamine[12] receptors are encoded by genes which contain introns. Our current data on the rate $D_2$ receptor now provides the first example of G-protein-coupled receptor isoforms which am generated through alternative RNA splicing. These isoforms am defined by the presence or absence of an internal 29 amino acid sequence within the receptor protein. This variation could have arisen either through the existence of a "cassette exon" or through alternative internal acceptor or donor sites within the precursor mRNA[16].

The isolation and sequencing of the rat $D_2$ receptor gene will be required to distinguish among these possibilities. The location of this optional amino acid sequence is particularly intriguing as it occurs within the predicted 3rd cytoplasmic loop of the receptor[12]. Recent mutagenesis studies using the $\beta_2$-adrenergic catecholamine receptor have indicated that this region is highly involved in G protein-receptor coupling[17,18]. It is thus tempting to speculate that the two $D_2$ receptor isoforms are coupled to different G proteins thus resulting in the diversity of responses associated with $D_2$ receptor activation[4-7]. Further work involving the stable expression of the two $D_2$ receptor isoforms in cells exhibiting appropriate G protein-linked effector systems will be required to test this hypothesis.

BIBLIOGRAPHY

1. Creese, I. & Fraser, C. M., eds., *Receptor Biochemistry and Methodology: Dopamine Receptors.* Vol. 8, Alan R. Liss, Inc., New York (1987).
2. Kebabian, J. W. et al. *Trends Pharmacol.* 7, 96–99 (1986).
3. Freissmuth, M., Casey, P. J. & Gilman, A. G. *FASEB J.* 3, 2125–2132 (1989).
4. Creese, I., Sibley, D. R., Hamblin, M. W. & Left. S. E. *Ann. Rev. Neurosci.* 6, 43–71 (1983).
5. Vallar, L. & Meldolesi, J. *Trends Pharmacol.* 10, 74–77 (1989).
6. Lacey, M. G., Mercuri, N. B. & North, R. A. *J. Physiol.* 392, 397–416 (1987).
7. Bigomia, L. et al. *J. Neurochem.* 51, 999–1006 (1988).
8. Senogles, S. E. et al. *J. Biol. Chem.* 262, 4860–4867 (1987).
9. Elazar, Z., Siegel, G. & Fuches, S. *EMBO J.* 8, 2353–2357 (1989).
10. Senogles. S. E., Amlaiky, N., Falardeau, P. & Caren, M. G. *J. Biol. Chem.* 263, 18995–19002 (1988).
11. Ohara, K. et al. *Mol. Pharm.* 33, 290–296 (1988).
12. Bunzow, J. R. et al. *Nature* 336, 783–787 (1988).
13. O'Dowd, B. F., Lefkowitz, R. J. & Caron, M. G. *Ann. Rev. Neurosci.* 12, 67–83 (1989).
14. Mount, S. M. *Nucleic Acids Res.* 10, 459–472 (1982).
15. Sibley, D. R., De Lean, A. & Creese, I. *J. Biol Chem.* 257, 6352–6361 (1982).
16. Andreadis, A., Gallego, M. E., Nadal-Ginard, B. *Ann. Rev. Cell Biol.* 3, 207–242 (1987),
17. Strader, C. D., Sigal, I. S. & Dixon, R. A. F. *FASEB J.* 3, 1825–1832 (1989).
18. O'Dowd, B. F. et al *J. Biol. Chem.* 263, 15985–15992 (1988).
19. Okayama, H. et al. *Methods Enzymol.* 154, 3–28 (1987).
20. Monsma, F. J., Jr., Brassard, D. L. & Sibley. D. R. *Brain Res.* 492, 214–324 (1989).
21. Gerfen, C. R. & Young, W. S. *Brain Res.* 460, 161–167 (1988).

For purposes of completing the background description and present disclosure, each of the published articles, patents and patent applications heretofore identified in this specification am hereby incorporated by reference into the specification, The foregoing invention has been described in some detail for purposes of clarity and understanding. It will also be obvious to one of ordinary skill in the art of genetic engineering that various combinations in form and detail can be made without departing from the scope of the invention.

What is claimed is:

1. A method of screening compounds for binding activity on the long isoform of mammalian D2 dopamine receptors comprising an amino acid sequence 242–270 shown in FIG. 1 of this specification, comprising the steps of transfecting an isolated cDNA segment into eukaryotic cells, said isolated cDNA segment encoding the long isoform of the mammalian D2 dopamine receptor comprising said amino acid sequence 242–270 and being operably linked with an expression vector;

harvesting said transfected eukaryotic cells;

treating said harvested eukaryotic cells with a labelled compound; and measuring amount of said labelled compound bound to said dopamine receptors on said eukaryotic cells.

2. The method of claim 1 wherein said labelled compound is radiolabelled.

3. The method of claim 1 wherein said labelled compound is fluorescently labelled.

* * * * *

UNITED STATES PATENT AND TRADEMARK OFFICE
CERTIFICATE OF CORRECTION

PATENT NO.    : 5,552,289
DATED         : September 3, 1996
INVENTOR(S)   : Sibley et al.

It is certified that error appears in the above-identified patent and that said Letters Patent is hereby corrected as shown below:

<u>Column 6,</u>
Line 62, delete "labelled" and insert -- labeled --
Line 63, delete "radiolabelled" and insert -- radiolabeled --
Lines 64 and 65, delete "labelled" and insert -- labeled --

Signed and Sealed this

Twenty-fifth Day of November, 2003

JAMES E. ROGAN
*Director of the United States Patent and Trademark Office*